United States Patent
Licht et al.

(10) Patent No.: US 9,743,968 B2
(45) Date of Patent: Aug. 29, 2017

(54) LOCKING MECHANISM FOR PECTUS BAR

(71) Applicant: Zimmer Biomet CMF and Thoracic, LLC, Jacksonville, FL (US)

(72) Inventors: James Licht, Jacksonville, FL (US); Pere Ventura, Jacksonville, FL (US); Max Billard, Ponte Vedra, FL (US); Shawn Robinson, Fleming Island, FL (US); Ryan Luby, Atlantic Beach, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 638 days.

(21) Appl. No.: 14/080,058

(22) Filed: Nov. 14, 2013

(65) Prior Publication Data
US 2015/0134009 A1     May 14, 2015

(51) Int. Cl.
*A61B 17/80* (2006.01)

(52) U.S. Cl.
CPC ...... *A61B 17/8076* (2013.01); *A61B 17/8014* (2013.01); *A61B 17/8061* (2013.01); *A61B 17/8085* (2013.01)

(58) Field of Classification Search
CPC . A61B 17/80; A61B 17/8052; A61B 17/8076; A61B 17/8085; F16B 39/284; Y10T 24/309; Y10T 24/301–24/303; Y10T 24/44026
USPC ...... 606/70–71, 280–321; 411/324, 325, 301
See application file for complete search history.

(56) References Cited

U.S. PATENT DOCUMENTS

| | | | |
|---|---|---|---|
| 212,242 A | 2/1879 | Loper | |
| 2,616,328 A | 11/1952 | Kingsmore | |
| 3,946,728 A | 3/1976 | Bettex | |
| 4,082,332 A | 4/1978 | Palmer | |
| 4,201,215 A | 5/1980 | Crossett et al. | |

(Continued)

FOREIGN PATENT DOCUMENTS

| | | |
|---|---|---|
| EP | 0583520 A1 | 2/1994 |
| WO | 2004028412 A1 | 4/2004 |

OTHER PUBLICATIONS

European Search Report for European Patent Application No. 06009368, dated Sep. 15, 2006.
(Continued)

*Primary Examiner* — Todd E Manahan
*Assistant Examiner* — Jessica Weiss
(74) *Attorney, Agent, or Firm* — Schwegman Lundberg & Woessner, P.A.

(57) ABSTRACT

A surgical implant may include a first implant member, a second implant member and a fastener. The first implant member may include a first aperture having first and second ends. The first aperture may include a female threaded portion and a barrier member disposed between the first and second ends and extending radially inward into the first aperture. The female threaded portion may be disposed between the first end and the barrier member. The second implant member may include a second aperture. The fastener may extend at least partially through the first and second apertures and may include a head portion and a shaft portion. The shaft portion may include a flexible tab and a male threaded portion engaging the female threaded portion. The male threaded portion may be disposed between the flexible tab and the head portion.

20 Claims, 3 Drawing Sheets

(56) References Cited

U.S. PATENT DOCUMENTS

| | | | |
|---|---|---|---|
| 4,202,327 A | 5/1980 | Glancy | |
| 4,327,715 A | 5/1982 | Corvisier | |
| 5,605,364 A | 2/1997 | Shelledy | |
| 5,755,808 A | 5/1998 | DeCarlo et al. | |
| 6,005,018 A | 12/1999 | Cicierega et al. | |
| 6,007,538 A | 12/1999 | Levin | |
| 6,010,503 A * | 1/2000 | Richelsoph | A61B 17/7032 606/278 |
| 6,024,759 A * | 2/2000 | Nuss | A61B 17/68 606/237 |
| 6,306,136 B1 | 10/2001 | Baccelli | |
| 6,355,038 B1 | 3/2002 | Pisharodi | |
| 6,656,179 B1 | 12/2003 | Schaefer et al. | |
| 6,689,134 B2 | 2/2004 | Ralph et al. | |
| 6,804,864 B2 | 10/2004 | Kirchen et al. | |
| 6,872,210 B2 | 3/2005 | Hearn | |
| 7,143,912 B2 * | 12/2006 | Caneba | A45C 13/262 224/153 |
| 7,785,332 B2 * | 8/2010 | Zannis | A61B 17/0401 606/139 |
| 7,950,887 B2 * | 5/2011 | Dietz | F16B 25/0021 411/301 |
| 8,353,939 B2 | 1/2013 | Anderson | |
| 2002/0106261 A1 | 8/2002 | Nakanishi | |
| 2002/0143336 A1 | 10/2002 | Hearn | |
| 2004/0116931 A1 | 6/2004 | Carlson | |
| 2004/0117016 A1 * | 6/2004 | Abramson | A61B 17/8076 623/16.11 |
| 2004/0204713 A1 | 10/2004 | Abdou | |
| 2005/0124996 A1 * | 6/2005 | Hearn | A61B 17/8009 606/71 |
| 2006/0058786 A1 | 3/2006 | Kim et al. | |
| 2006/0089648 A1 | 4/2006 | Masini | |
| 2006/0259141 A1 | 11/2006 | Roman et al. | |
| 2008/0319484 A1 * | 12/2008 | Fauth | A61F 2/4405 606/247 |
| 2010/0106189 A1 | 4/2010 | Miller | |
| 2010/0114170 A1 | 5/2010 | Barrus et al. | |
| 2011/0022097 A1 | 1/2011 | Walker et al. | |
| 2011/0142565 A1 | 6/2011 | Pudvah | |
| 2011/0160779 A1 * | 6/2011 | Schlaepfer | A61B 17/7035 606/305 |
| 2012/0172934 A1 * | 7/2012 | Fisher | A61B 17/844 606/304 |
| 2013/0096636 A1 * | 4/2013 | Courtney | A61B 17/7037 606/308 |
| 2013/0211465 A1 * | 8/2013 | Savage | A61B 17/7037 606/308 |
| 2014/0094856 A1 * | 4/2014 | Sinha | A61B 17/8042 606/291 |

OTHER PUBLICATIONS

U.S. Office Action regarding U.S. Appl. No. 11/402,319 mailed Feb. 23, 2009.

U.S. Office Action regarding U.S. Appl. No. 11/402,319 mailed Aug. 5, 2009.

* cited by examiner

LOCKING MECHANISM FOR PECTUS BAR

FIELD

The present disclosure relates to a locking mechanism for a pectus bar.

BACKGROUND

This section provides background information related to the present disclosure and is not necessarily prior art.

Surgical procedures may be conducted to correct chest wall deformities such as pectus excavatum or pectus carinatum. Such surgical procedures may utilize a pectus bar assembly to reshape the patient's chest wall. A first surgical procedure may include implanting the pectus bar assembly into the patient's body. The pectus bar assembly may remain within the patient's body for a period of time (e.g., months or years) before a subsequent surgical procedure is conducted to remove the pectus bar assembly from the patient's body. Assembly of the pectus bar assembly during the first surgical procedure and/or disassembly of the pectus bar assembly during the second surgical procedure may occur within the surgical site. Therefore, ease of use of the pectus bar assembly is desirable.

The pectus bar assembly may include a pectus bar and one or more stabilizers mounted to a supporting structure (e.g., muscle, cartilage, bone and/or any other type of tissue) within the patient's body. The pectus bar may be secured to the one or more stabilizers using one or more fasteners.

SUMMARY

This section provides a general summary of the disclosure, and is not a comprehensive disclosure of its full scope or all of its features.

In one form, the present disclosure provides a surgical implant that may include a first implant member, a second implant member and a fastener. The first implant member may be configured to be configured to be implanted within a human body and may include a first aperture having first and second ends. The first aperture may include a female threaded portion and a barrier member disposed between the first and second ends and extending radially inward into the first aperture. The female threaded portion may be disposed between the first end and the barrier member. The second implant member may be configured to be implanted within the human body and may include a second aperture. The fastener may be configured to be implanted within the human body and may extend at least partially through the first and second apertures and may include a head portion and a shaft portion. The shaft portion may include a flexible tab and a male threaded portion engaging the female threaded portion. The male threaded portion may be disposed between the flexible tab and the head portion.

In some embodiments, the flexible tab may include a barbed tip that extends radially outward.

In some embodiments, the barrier member may include an annular ridge having a first diameter.

In some embodiments, the first diameter may be less than major and minor thread diameters of the female threaded portion.

In some embodiments, the shaft portion may include a plurality of flexible tabs having barbed tips that define a second diameter that is greater than the first diameter.

In some embodiments, the second diameter may be less than the major and minor thread diameters of the female threaded portion.

In some embodiments, the annular ridge may be disposed between the barbed tips and the male threaded portion of the fastener when the fastener is fully engaged with the first implant member.

In some embodiments, the second aperture of the second implant member may include at least one of a counterbore and a countersink that at least partially receives the head portion of the fastener.

In some embodiments, a distal end of the shaft portion may be disposed within the first aperture when the fastener is fully engaged with the first implant member.

In some embodiments, the first aperture of the first implant member may include a recessed portion. The barrier member may be disposed between the recessed portion and the threaded portion. Barbed tips of the flexible tabs of the fastener may be received within the recessed portion when the fastener is fully seated within the first and second apertures.

In some embodiments, the first implant member may be a stabilizer plate and the second implant member may be a pectus bar.

In some embodiments, the first implant member may be attached to a supporting structure (e.g., muscle, cartilage, bone and/or any other type of tissue) within the patient's body. Additionally or alternatively, the second implant member may be attached to the supporting structure within the patient's body.

In some embodiments, neither of the first and second implant members are fixedly attached to a supporting structure within the human body after being implanted into the human body.

In another form, the present disclosure provides a surgical method that may include providing a first implant member including a first aperture having a female threaded portion and a barrier member. A second aperture of a second implant member may be aligned with the first aperture. A fastener may be provided that includes a shaft having a male threaded portion and a barb at a distal end of the shaft. The fastener may be inserted through the second aperture and into the first aperture. A first torque may be applied to the fastener until the barb passes the barrier member. A second torque may be applied to the fastener after the barb has passed the barrier member to threadably advance the fastener into the first aperture. The second torque may be less than the first torque. The second implant member may be clamped between a head of the fastener and the first implant member by applying a third torque to the fastener that is greater than the second torque.

In some embodiments, the first implant member may be attached to the a supporting structure (e.g., muscle, cartilage, bone and/or any other type of tissue) within the patient's body after the second implant member is secured to the first implant member. In other embodiments, the first implant member may be attached to the supporting structure before the second implant member is secured to the first implant member.

In some embodiments, only the second implant member may be directly secured to the supporting structure before and/or after being secured to the first implant member. In some embodiments, neither of the first and second implant members may be fixedly secured to a supporting structure within the patient's body.

In some embodiments, the third torque may be greater than the first torque.

In some embodiments, the surgical method may include threadably advancing the fastener to a location at which the barb is in contact with the barrier member prior to applying the first torque.

In some embodiments, the barrier member may include an annular ridge having a first diameter.

In some embodiments, the first diameter may be less than major and minor thread diameters of the female threaded portion.

In some embodiments, the shaft may include a plurality of barbs that define a second diameter that is greater than the first diameter.

In some embodiments, the second diameter may be less than the major and minor thread diameters of the female threaded portion.

In some embodiments, the annular ridge may be disposed between the barbs and the male threaded portion of the fastener when the second implant member is clamped between the head of the fastener and the first implant member.

In some embodiments, the first implant member may be a stabilizer plate and the second implant member may be a pectus bar.

In some embodiments, the head of the fastener may be at least partially received within one of a countersink and a counterbore of the second implant member when the second implant member is clamped between the head of the fastener and the first implant member.

In some embodiments, a distal end of the fastener may be disposed within the first aperture when the second implant member is clamped between the head of the fastener and the first implant member.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
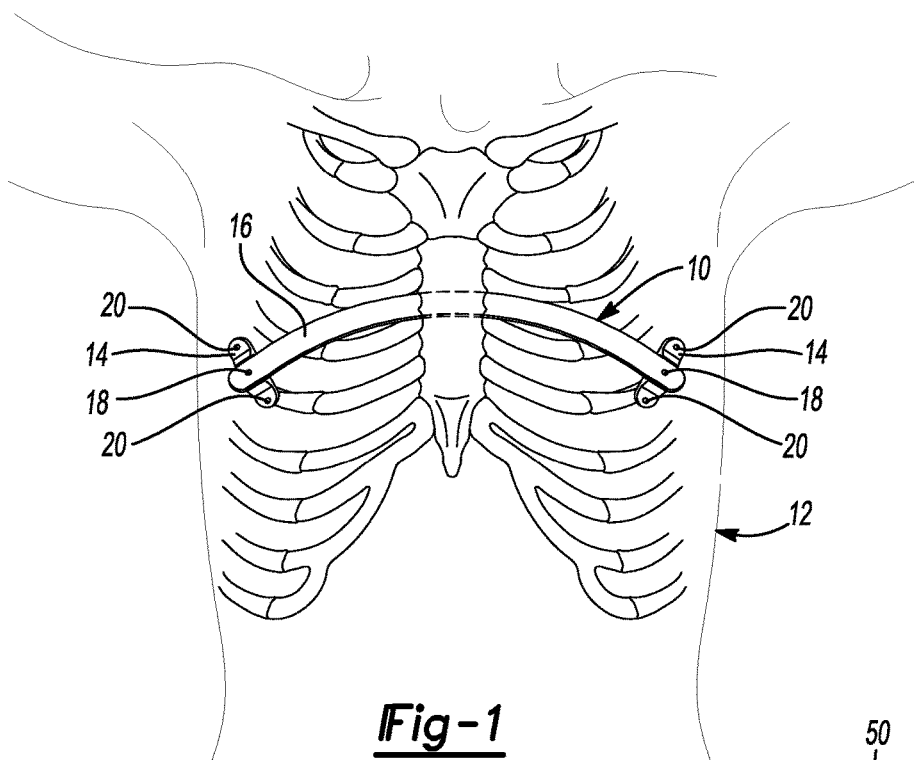
FIG. 1 is a perspective view of a torso of a human body having a pectus bar assembly attached thereto according to the principles of the present disclosure.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIGS. 1-5, a pectus bar assembly 10 is provided that may be surgically implanted into a patient's body 12. The pectus bar assembly 10 may be used to correct to a chest wall deformity such as pectus excavatum or pectus carinatum, for example. As will be subsequently described, the pectus bar assembly 10 may be implanted into the patient's body 12 during a first surgical procedure in which the pectus bar assembly 10 may be mounted to supporting structure (e.g., cartilage and/or bone) within the patient's body 12. The pectus bar assembly 10 may remain within the patient's body 12 for a period of time (e.g., months or years) before a subsequent surgical procedure is conducted to remove the pectus bar assembly 10 from the patient's body 12.

The pectus bar assembly 10 may include one or more stabilizers 14, a pectus bar 16 and one or more first fasteners 18 and a plurality of second fasteners 20. While FIG. 1 depicts the pectus bar assembly 10 having two stabilizers 14, in some embodiments, only a single stabilizer 14 may be employed. Each stabilizer 14 may include first and second end portions 22, 24 and a central portion 26. The first and second end portions 22, 24 may each include a mounting aperture 28 through which the second fasteners 20 (FIG. 1) may be inserted to secure the stabilizer 14 to the patient's body 12. The second portion 26 may include a pair of ramped portions 30 defining a channel 32 therebetween.

Figure 3:
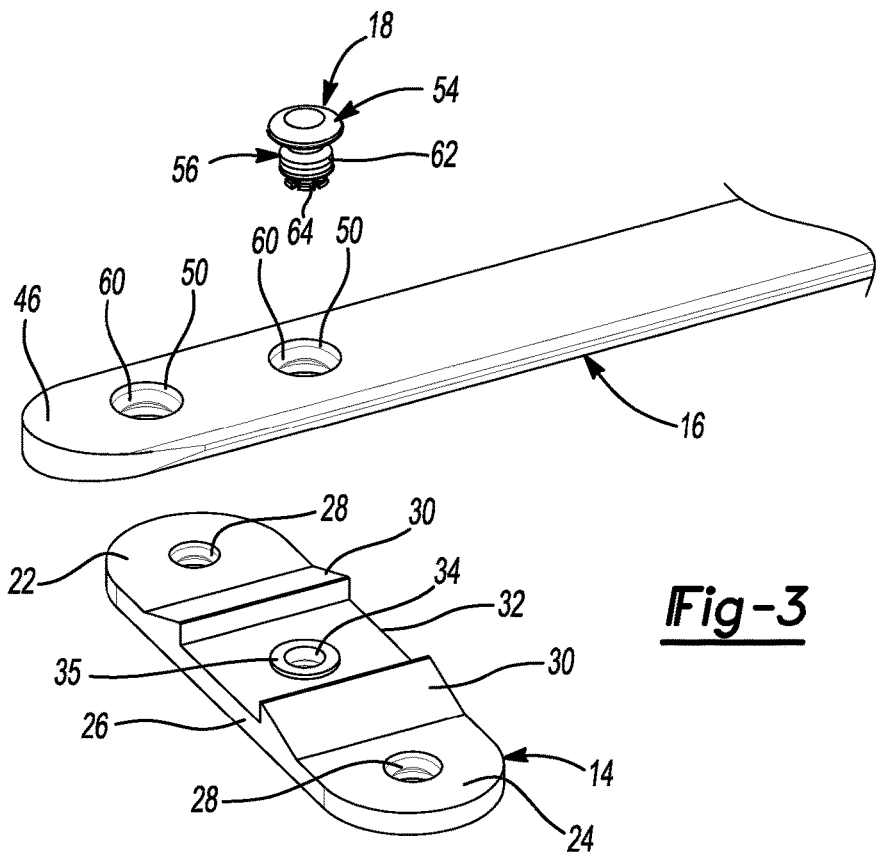
FIG. 3 is an exploded partial perspective view of the pectus bar assembly.
Figure 4:
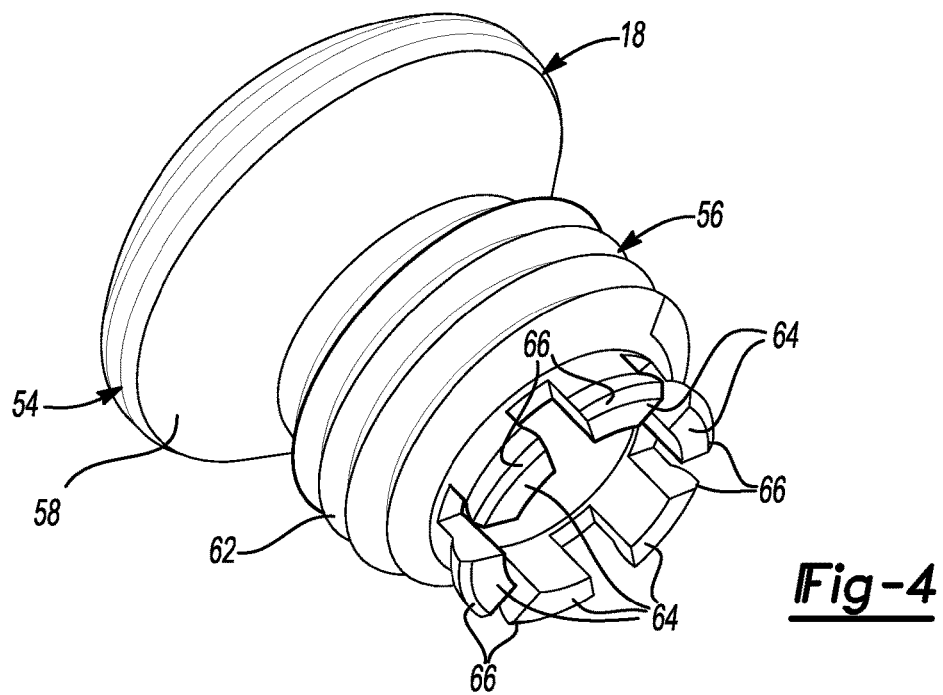
FIG. 4 is a perspective view of a fastener of the pectus bar assembly.
Figure 5:
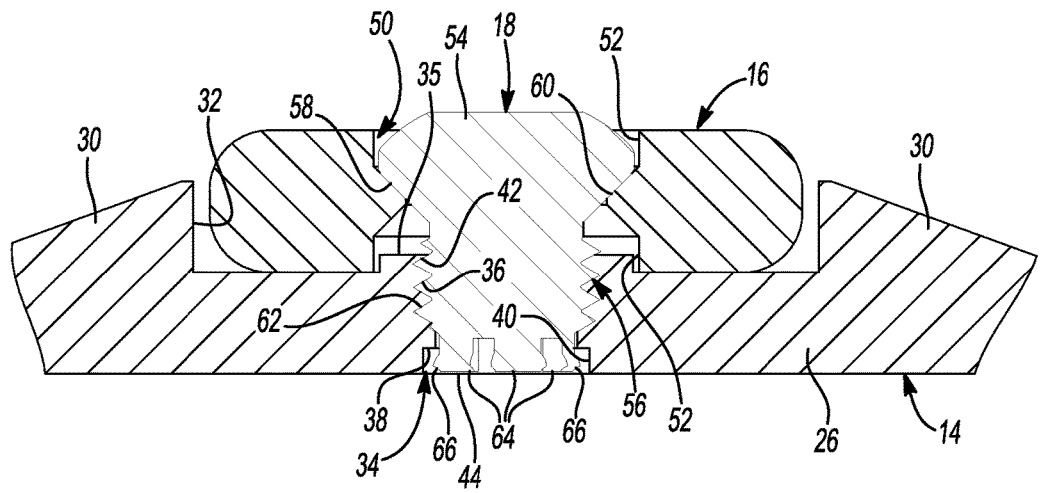
FIG. 5 is a partial cross-sectional view of the pectus bar assembly taken along line 5-5 of FIG. 2.

As shown in FIGS. 3 and 5, an aperture 34 may be disposed in the recess and may extend through the central portion 26. In some embodiments, a raised annular boss 35 may surround the aperture 34. As shown in FIG. 5, the aperture 34 may include a female threaded portion 36, a barrier member 38 and a recessed portion 40. The threaded portion 36 may extend axially from a first end 42 of the aperture 34 to the barrier member 38. The recessed portion 40 may extend axially from the barrier member 38 to a second end 44 of the aperture 34. The barrier member 38 may be an annular ridge that extends radially inward into the aperture 34. The barrier member 38 may have an inner diameter that is less than major and minor thread diameters of the threaded portion 36. The recessed portion 40 may include an inner diameter that is greater than the inner diameter of the barrier member 38. In some embodiments, the inner diameter of the recessed portion 40 may be greater than one or both of the major and minor thread diameters of the threaded portion 36.

Figure 2:
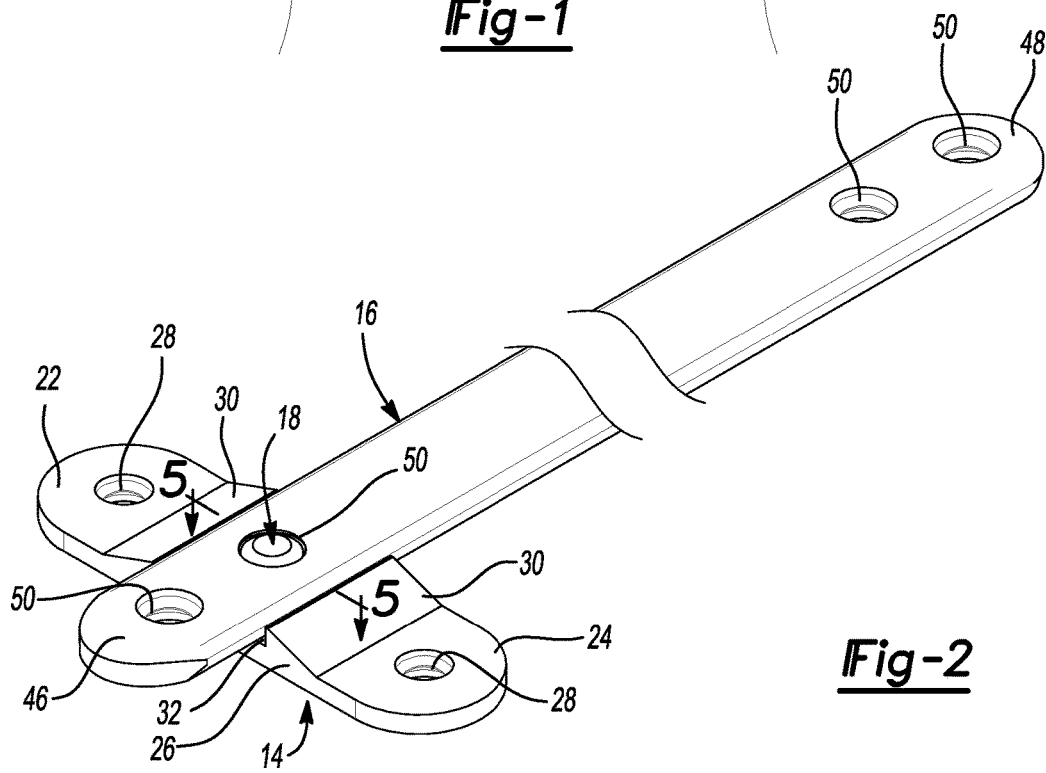
FIG. 2 is a partial perspective view of the pectus bar assembly.

The pectus bar 16 may be an elongated member having first and second end portions 46, 48 (FIG. 2). The pectus bar 16 may include a first group of apertures 50 disposed generally proximate the first end 46 and a second group of apertures 50 disposed generally proximate the second end 48. While FIG. 2 depicts the first and second end portions 46, 48 each including a pair of apertures 50, it will be appreciated that each of the first and second end portions 46, 48 could include any number of apertures 50. One or both axial ends of each aperture 50 may include a counterbored and/or countersunk portion 52. The pectus bar 16 may be received in the channel 32 of the stabilizer 14 and may be positioned therein such that a selected one of the apertures 50 is axially aligned with the aperture 34 in the stabilizer 14. As shown in FIG. 5, the raised annular boss 35 of the stabilizer 14 may be received in one of the countersunk portions 52 of the selected aperture 50. As shown in FIGS. 2 and 5, the fastener 18 may extend through the selected aperture 50 of the pectus bar 16 and engage the aperture 34 in the stabilizer 14. In some embodiments, plugs (not shown) may be used to fill the unused apertures 50 in the pectus bar 16.

The fastener 18 may include a head portion 54 and a shaft portion 56. The head portion 54 may be sized to be at least partially received in the countersunk portion 52 of the apertures 50 in the pectus bar 16. As shown in FIG. 5, a tapered surface 58 of the head portion 54 adjacent the shaft portion 56 may abut a tapered surface 60 of the aperture 50.

The shaft portion 56 may include a threaded portion 62 and an axial end having a plurality of resiliently flexible tabs 64. The threaded portion 62 of the fastener 18 may threadably engage the threaded portion 36 of the aperture 34 of the stabilizer 14. Each of the tabs 64 may extend axially downward from the threaded portion 62. The tabs 64 may be angularly spaced apart from each other. Each of the tabs 64 may include a barb 66 that extends radially outward from a tip of the tab 64. The barbs 66 may cooperate with each other to define a diameter that is larger than the inner diameter of the barrier member 38 when the tabs 64 are in a relaxed (non-flexed) state (FIG. 5). As the fastener 18 is threadably advanced through the aperture 34 of the stabilizer 14, interference between the barrier member 38 and the tabs 64 may resiliently flex the tabs 64 radially inward to allow the tabs 64 to pass through the barrier member 38. Once the barbs 66 of the tabs 64 pass the barrier member 38 (i.e., so that the barrier member 38 is axially between the barbs 66 and the threaded portion 62) the tabs 64 may spring back to the relaxed or non-flexed state (shown in FIG. 5).

With reference to FIGS. 1-6, a surgical method using the pectus bar assembly 10 will be described. A surgeon may bend the pectus bar 16 into an arch shape (as shown in FIG. 1). The curvature of the arch shape may be selected by the surgeon based on the type and severity of the patient's deformity. The surgeon may make an incision in the patient's body 12 and insert the pectus bar 16 and one or more stabilizers 14 therethrough. The pectus bar 16 may be secured to the one or more stabilizers 14 before or after being inserted into the patient's body. In some embodiments (e.g., in a procedure for correcting a pectus excavatum condition), the one or more stabilizers 14 may be secured to a supporting structure within the patient's body (e.g., the patient's muscle, cartilage, bone and/or other tissue) after the pectus bar 16 is attached to the stabilizer(s) 14. In some embodiments (e.g., in a procedure for correcting a pectus carinatum condition), the one or more stabilizers 14 may be secured to the patient's muscle, cartilage, bone and/or other tissue before the pectus bar 16 is attached to the stabilizer(s) 14.

To attach the pectus bar 16 to the stabilizer 14, the pectus bar 16 may be positioned within the channel 32 of the stabilizer 14 such that the aperture 50 is axially aligned with the aperture 34 in the stabilizer 14. The raised annular boss 35 of the stabilizer 14 may provide tactile feedback to the surgeon indicating axial alignment between the apertures 34, 50, as the boss 35 is received in one of the countersunk portions 52 of the aperture 50 when the boss 35 and aperture 34 are axially aligned with the aperture 50.

Figure 6:
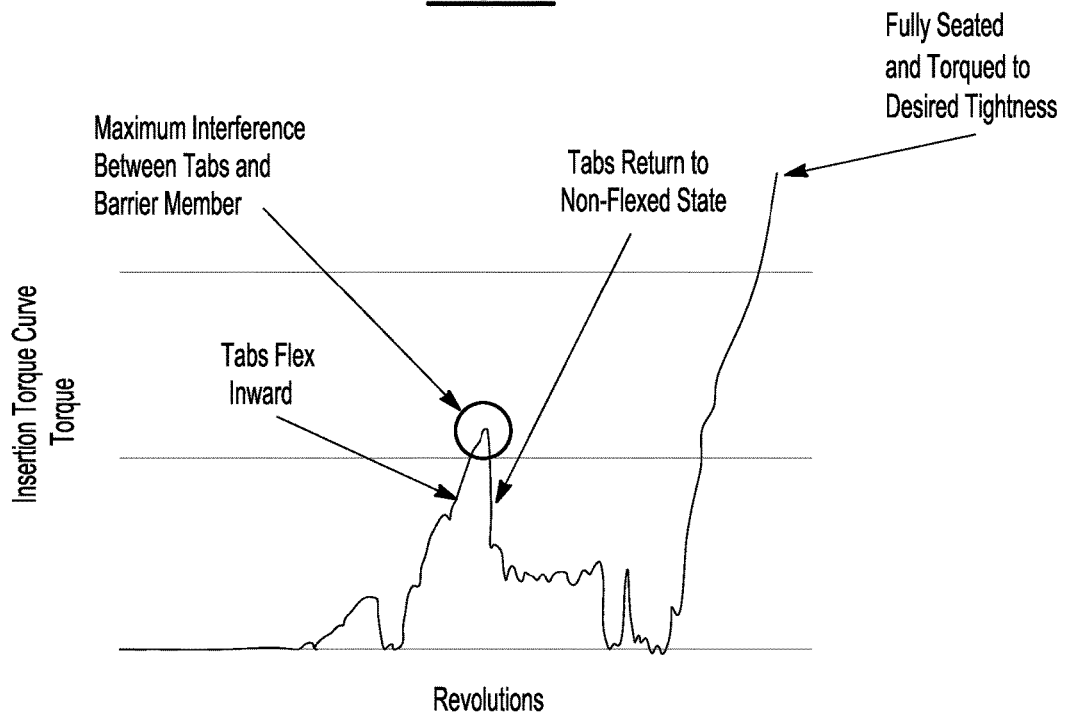
FIG. 6 is a graph of torque applied to the fastener during installation of the fastener into the pectus bar assembly.

Once the apertures 34, 50 are axially aligned with each other, the fastener 18 may be inserted through the aperture 50 in the pectus bar 16 and into the aperture 34 of the stabilizer 14. The surgeon may apply a torque to the fastener 18 (using a screwdriver or wrench, for example) to threadably advance the threaded portion 62 of the fastener 18 along the threaded portion 36 of the aperture 34. As the fastener 18 continues to be advanced through the aperture 34, the tabs 64 of the fastener 18 will come into contact with the barrier member 38 in the aperture 34. After initial contact between the tabs 64 and the barrier member 38, continued advancement of the fastener 18 through the aperture 34 will flex the tabs 64 radially inward. As shown in FIG. 6, the magnitude of the torque that the surgeon applies to the fastener 18 to continue advancing the fastener 18 through the aperture 34 after initial contact between the tabs 64 and the barrier member 38 continues to increase until the radially outermost edge of the barbs 66 of the tabs 64 are engaged with the radially innermost surface of the barrier member 38 (i.e., when the tabs 64 are at their maximum inwardly flexed state).

Once the barbs 66 of the tabs 64 pass the barrier member 38, the tabs 64 resiliently return to their non-flexed state as the surgeon continues to threadably advance the fastener 18 through the aperture 34. The torque necessary for advancing the fastener 18 once the tabs 64 begin to unflex may be less than the torque necessary for advancing the fastener 18 while the tabs 64 are flexing inward, as shown in FIG. 6. Thereafter, the tapered surface 58 of the head portion 54 of the fastener 18 may seat against the tapered surface 60 of the countersunk portion 52 of the aperture 50. The surgeon may torque the fastener 18 to a desired tightness to clamp the pectus bar 16 against the stabilizer 14. In some embodiments, it may be necessary for the surgeon to apply a greater torque to the fastener 18 to sufficiently tighten the fastener 18 than the torque applied to flex the tabs 64 inward.

As shown in FIG. 5, once the fastener 18 is seated against the tapered surface 60 of the aperture 50, the head portion 54 may be partially or completely received in the countersunk portion 52 of the aperture 50, thereby lowering the profile (thickness) of the pectus bar assembly 10 within the patient's body 12. The relatively large amount of torque that may be necessary to flex the tabs 64 inward to a sufficient extent to allow the fastener 18 to be removed from the aperture 34 allows for the pectus bar 16 to be secured to the stabilizer 14 without using a locking washer, a nut or other hardware that is typically used to ensure threaded fasteners do not back out of threaded holes.

While the fastener 18 is described above as including the flexible tabs 64 and the stabilizer 14 is described as including the barrier member 38, in some embodiments, the fastener 18 could include a barrier member and the stabilizer 14 could include one or more flexible or compressible members that interact with the barrier member on the fastener 18 in a similar manner as described above.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical implant comprising:
a first implant member configured to be implanted within a human body and including a first surface, a second surface, and a first aperture extending from the first surface to the second surface, the first aperture including a female threaded portion and a barrier member disposed between the first and second surfaces and extending radially inward into the first aperture, the female threaded portion disposed between the first surface and the barrier member;
a second implant member configured to be implanted within the human body and including a second aperture; and
a fastener configured to be implanted within the human body and extend at least partially through the first and second apertures, the fastener including a head portion and a shaft portion having a flexible tab and a male threaded portion, the male threaded portion disposed between the flexible tab and the head portion and configured to engage the female threaded portion, the flexible tab configured to engage the barrier member, wherein the first implant member is a stabilizer plate and the second implant member is a pectus bar.

2. The surgical implant of claim 1, wherein the flexible tab includes a barbed tip that extends radially outward.

3. The surgical implant of claim 2, wherein the barrier member includes an annular ridge having a first diameter.

4. The surgical implant of claim 3, wherein the first diameter is less than major and minor thread diameters of the female threaded portion.

5. The surgical implant of claim 4, wherein the shaft portion includes a plurality of flexible tabs having barbed tips that define a second diameter that is greater than the first diameter.

6. The surgical implant of claim 5, wherein the second diameter is less than the major and minor thread diameters of the female threaded portion.

7. The surgical implant of claim 5, wherein the annular ridge is disposed between the barbed tips and the male threaded portion of the fastener when the fastener is fully engaged with the first implant member.

8. The surgical implant of claim 1, wherein the second aperture of the second implant member includes at least one of a counterbore and a countersink that at least partially receives the head portion of the fastener.

9. The surgical implant of claim 8, wherein a distal end of the shaft portion is disposed within the first aperture when the fastener is fully engaged with the first implant member.

10. A surgical method comprising:
providing a first implant member including a first aperture having a female threaded portion and a barrier member;
aligning a second aperture of a second implant member with the first aperture wherein the first implant member is a stabilizer plate and the second implant member is a pectus bar;
providing a fastener including a shaft having a male threaded portion and a barb at a distal end of the shaft;
inserting the fastener through the second aperture and into the first aperture;
applying a first torque to the fastener until the barb passes the barrier member;
applying a second torque to the fastener after the barb has passed the barrier member to threadably advance the fastener into the first aperture, the second torque being less than the first torque; and
clamping the second implant member between a head of the fastener and the first implant member by applying a third torque to the fastener that is greater than the second torque.

11. The surgical method of claim 10, wherein the third torque is greater than the first torque.

12. The surgical method of claim 10, further comprising threadably advancing the fastener to a location at which the barb is in contact with the barrier member prior to applying the first torque.

13. The surgical method of claim 10, wherein the barrier member includes an annular ridge having a first diameter.

14. The surgical method of claim 13, wherein the first diameter is less than major and minor thread diameters of the female threaded portion.

15. The surgical method of claim 14, wherein the shaft includes a plurality of barbs that define a second diameter that is greater than the first diameter.

16. The surgical method of claim 15, wherein the second diameter is less than the major and minor thread diameters of the female threaded portion.

17. The surgical method of claim 15, wherein the annular ridge is disposed between the barbs and the male threaded portion of the fastener when the second implant member is clamped between the head of the fastener and the first implant member.

18. The surgical method of claim 10, wherein the head of the fastener is at least partially received within one of a countersink and a counterbore of the second implant member when the second implant member is clamped between the head of the fastener and the first implant member.

19. The surgical method of claim 18, wherein a distal end of the fastener is disposed within the first aperture when the second implant member is clamped between the head of the fastener and the first implant member.

20. The surgical method of claim 10, further comprising attaching at least one of the first and second implant members to tissue.

\* \* \* \* \*

UNITED STATES PATENT AND TRADEMARK OFFICE
CERTIFICATE OF CORRECTION

| | |
|---|---|
| PATENT NO. | : 9,743,968 B2 |
| APPLICATION NO. | : 14/080058 |
| DATED | : August 29, 2017 |
| INVENTOR(S) | : Licht et al. |

It is certified that error appears in the above-identified patent and that said Letters Patent is hereby corrected as shown below:

In the Claims

In Column 8, Line 45, in Claim 10, after "aperture", insert --,--

Signed and Sealed this
Twenty-seventh Day of March, 2018

Andrei Iancu
*Director of the United States Patent and Trademark Office*